United States Patent
Wong et al.

(10) Patent No.: US 7,887,345 B2
(45) Date of Patent: Feb. 15, 2011

(54) SINGLE USE CONNECTOR FOR PULSE OXIMETRY SENSORS

(75) Inventors: Marvin Wong, Fremont, CA (US); Albert Ollerdessen, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 12/165,166

(22) Filed: Jun. 30, 2008

(65) Prior Publication Data

US 2009/0325408 A1 Dec. 31, 2009

(51) Int. Cl.
*H01R 13/44* (2006.01)
(52) U.S. Cl. ...................... 439/140; 439/258
(58) Field of Classification Search ............. 439/258, 439/180, 166, 160, 159, 140, 141, 923
See application file for complete search history.

(56) References Cited

U.S. PATENT DOCUMENTS

| | | | |
|---|---|---|---|
| 3,721,813 | A | 3/1973 | Condon et al. |
| 4,586,513 | A | 5/1986 | Hamaguri |
| 4,603,700 | A | 8/1986 | Nichols et al. |
| 4,621,643 | A | 11/1986 | New, Jr. et al. |
| 4,653,498 | A | 3/1987 | New, Jr. et al. |
| 4,685,464 | A | 8/1987 | Goldberger et al. |
| 4,694,833 | A | 9/1987 | Hamaguri |
| 4,697,593 | A | 10/1987 | Evans et al. |
| 4,700,708 | A | 10/1987 | New, Jr. et al. |
| 4,714,080 | A | 12/1987 | Edgar, Jr. et al. |
| 4,714,341 | A | 12/1987 | Hamaguri et al. |
| 4,759,369 | A | 7/1988 | Taylor |
| 4,770,179 | A | 9/1988 | New, Jr. et al. |
| 4,773,422 | A | 9/1988 | Isaacson et al. |
| 4,776,339 | A | 10/1988 | Schreiber |
| 4,781,195 | A | 11/1988 | Martin |

(Continued)

FOREIGN PATENT DOCUMENTS

DE 3703458 8/1988

(Continued)

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

(Continued)

*Primary Examiner*—T C Patel
*Assistant Examiner*—Phuong Nguyen
(74) *Attorney, Agent, or Firm*—Fletcher Yoder

(57) ABSTRACT

This disclosure describes systems and methods for a single-use oximetry sensor in which a single-use connector is used with the sensor assembly. The disclosure describes a connector which consists of a single-use male connector for use with female connector on an oximeter. The connector includes a housing enclosing one or more pins, one or more movable members, and a locking mechanism. Upon engagement of the male connector into the female connector the locking mechanism activates such that when the female connector is removed, the moveable member moves from a first position to a second position and locks into the second position. When in the second position the male connector can not engage the female connector, thereby limiting the male connector to a single use engagement.

18 Claims, 3 Drawing Sheets

U.S. PATENT DOCUMENTS

| | | | |
|---|---|---|---|
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hausmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,040,039 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H01039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A * | 10/1993 | Goldberger et al. | 600/323 |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,145 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |

| | | | | | | |
|---|---|---|---|---|---|---|
| 5,398,680 A | 3/1995 | Polson et al. | | 5,645,440 A | 7/1997 | Tobler et al. |
| 5,402,777 A | 4/1995 | Warring et al. | | 5,660,567 A | 8/1997 | Nierlich et al. |
| 5,411,023 A | 5/1995 | Morris, Sr. et al. | | 5,662,105 A | 9/1997 | Tien |
| 5,411,024 A | 5/1995 | Thomas et al. | | 5,662,106 A | 9/1997 | Swedlow et al. |
| 5,413,099 A | 5/1995 | Schmidt et al. | | 5,666,952 A | 9/1997 | Fuse et al. |
| 5,413,100 A | 5/1995 | Barthelemy et al. | | 5,671,529 A | 9/1997 | Nelson |
| 5,413,101 A | 5/1995 | Sugiura | | 5,673,692 A | 10/1997 | Schulze et al. |
| 5,413,102 A | 5/1995 | Schmidt et al. | | 5,673,693 A | 10/1997 | Solenberger |
| 5,417,207 A | 5/1995 | Young et al. | | 5,676,139 A | 10/1997 | Goldberger et al. |
| 5,421,329 A | 6/1995 | Casciani et al. | | 5,676,141 A | 10/1997 | Hollub |
| 5,425,360 A | 6/1995 | Nelson | | 5,678,544 A | 10/1997 | DeLonzor et al. |
| 5,425,362 A | 6/1995 | Siker et al. | | 5,680,857 A | 10/1997 | Pelikan et al. |
| 5,427,093 A | 6/1995 | Ogawa et al. | | 5,685,299 A | 11/1997 | Diab et al. |
| 5,429,128 A | 7/1995 | Cadell et al. | | 5,685,301 A | 11/1997 | Klomhaus |
| 5,429,129 A | 7/1995 | Lovejoy et al. | | 5,687,719 A | 11/1997 | Sato et al. |
| 5,431,159 A | 7/1995 | Baker et al. | | 5,687,722 A | 11/1997 | Tien et al. |
| 5,431,170 A | 7/1995 | Mathews | | 5,692,503 A | 12/1997 | Kuenstner |
| 5,437,275 A | 8/1995 | Amundsen et al. | | 5,692,505 A | 12/1997 | Fouts |
| 5,438,986 A | 8/1995 | Disch et al. | | 5,709,205 A | 1/1998 | Bukta |
| 5,448,991 A | 9/1995 | Polson et al. | | 5,713,355 A | 2/1998 | Richardson et al. |
| 5,452,717 A | 9/1995 | Branigan et al. | | 5,724,967 A | 3/1998 | Venkatachalam |
| 5,465,714 A | 11/1995 | Scheuing | | 5,727,547 A | 3/1998 | Levinson et al. |
| 5,469,845 A | 11/1995 | DeLonzor et al. | | 5,731,582 A | 3/1998 | West |
| RE35,122 E | 12/1995 | Corenman et al. | | D393,830 S | 4/1998 | Tobler et al. |
| 5,482,034 A | 1/1996 | Lewis et al. | | 5,743,260 A | 4/1998 | Chung et al. |
| 5,482,036 A | 1/1996 | Diab et al. | | 5,743,263 A | 4/1998 | Baker, Jr. |
| 5,483,646 A | 1/1996 | Uchikoga | | 5,746,206 A | 5/1998 | Mannheimer |
| 5,485,847 A | 1/1996 | Baker, Jr. | | 5,746,697 A | 5/1998 | Swedlow et al. |
| 5,490,505 A | 2/1996 | Diab et al. | | 5,752,914 A | 5/1998 | DeLonzor et al. |
| 5,490,523 A | 2/1996 | Isaacson et al. | | 5,755,226 A | 5/1998 | Carim et al. |
| 5,491,299 A | 2/1996 | Naylor et al. | | 5,758,644 A | 6/1998 | Diab et al. |
| 5,494,032 A | 2/1996 | Robinson et al. | | 5,760,910 A | 6/1998 | Lepper, Jr. et al. |
| 5,497,771 A | 3/1996 | Rosenheimer | | 5,766,125 A | 6/1998 | Aoyagi et al. |
| 5,499,627 A | 3/1996 | Steuer et al. | | 5,766,127 A | 6/1998 | Pologe et al. |
| 5,503,148 A | 4/1996 | Pologe et al. | | 5,769,785 A | 6/1998 | Diab et al. |
| 5,505,199 A | 4/1996 | Kim | | 5,772,587 A | 6/1998 | Gratton et al. |
| 5,507,286 A | 4/1996 | Solenberger | | 5,774,213 A | 6/1998 | Trebino et al. |
| 5,517,988 A | 5/1996 | Gerhard | | 5,776,058 A | 7/1998 | Levinson et al. |
| 5,520,177 A | 5/1996 | Ogawa et al. | | 5,776,059 A | 7/1998 | Kaestle |
| 5,521,851 A | 5/1996 | Wei et al. | | 5,779,630 A | 7/1998 | Fein et al. |
| 5,522,388 A | 6/1996 | Ishikawa et al. | | 5,779,631 A | 7/1998 | Chance |
| 5,524,617 A | 6/1996 | Mannheimer | | 5,782,237 A | 7/1998 | Casciani et al. |
| 5,529,064 A | 6/1996 | Rall et al. | | 5,782,756 A | 7/1998 | Mannheimer |
| 5,533,507 A | 7/1996 | Potratz et al. | | 5,782,757 A | 7/1998 | Diab et al. |
| 5,551,423 A | 9/1996 | Sugiura | | 5,782,758 A | 7/1998 | Ausec et al. |
| 5,551,424 A | 9/1996 | Morrison et al. | | 5,786,592 A | 7/1998 | Hök |
| 5,553,614 A | 9/1996 | Chance | | 5,790,729 A | 8/1998 | Pologe et al. |
| 5,553,615 A | 9/1996 | Carim et al. | | 5,792,052 A | 8/1998 | Isaacson et al. |
| 5,555,882 A | 9/1996 | Richardson et al. | | 5,795,292 A | 8/1998 | Lewis et al. |
| 5,558,096 A | 9/1996 | Palatnik | | 5,797,841 A | 8/1998 | DeLonzor et al. |
| 5,560,355 A | 10/1996 | Merchant et al. | | 5,800,348 A | 9/1998 | Kaestle |
| 5,564,417 A | 10/1996 | Chance | | 5,800,349 A | 9/1998 | Isaacson et al. |
| 5,575,284 A | 11/1996 | Athan et al. | | 5,803,910 A | 9/1998 | Potratz |
| 5,575,285 A | 11/1996 | Takanashi et al. | | 5,807,246 A | 9/1998 | Sakaguchi et al. |
| 5,577,500 A | 11/1996 | Potratz | | 5,807,247 A | 9/1998 | Merchant et al. |
| 5,582,169 A | 12/1996 | Oda et al. | | 5,807,248 A | 9/1998 | Mills |
| 5,584,296 A | 12/1996 | Cui et al. | | 5,810,723 A | 9/1998 | Aldrich |
| 5,588,425 A | 12/1996 | Sackner et al. | | 5,810,724 A | 9/1998 | Gronvall |
| 5,588,427 A | 12/1996 | Tien | | 5,813,980 A | 9/1998 | Levinson et al. |
| 5,590,652 A | 1/1997 | Inai | | 5,817,008 A | 10/1998 | Rafert et al. |
| 5,595,176 A | 1/1997 | Yamaura | | 5,817,009 A | 10/1998 | Rosenheimer et al. |
| 5,596,986 A | 1/1997 | Goldfarb | | 5,817,010 A | 10/1998 | Hibl |
| 5,611,337 A | 3/1997 | Bukta | | 5,818,985 A | 10/1998 | Merchant et al. |
| 5,617,852 A | 4/1997 | MacGregor | | 5,820,550 A | 10/1998 | Polson et al. |
| 5,619,992 A | 4/1997 | Guthrie et al. | | 5,823,950 A | 10/1998 | Diab et al. |
| 5,626,140 A | 5/1997 | Feldman et al. | | 5,823,952 A | 10/1998 | Levinson et al. |
| 5,630,413 A | 5/1997 | Thomas et al. | | 5,827,182 A | 10/1998 | Raley et al. |
| 5,632,272 A | 5/1997 | Diab et al. | | 5,830,135 A | 11/1998 | Bosque et al. |
| 5,632,273 A | 5/1997 | Suzuki | | 5,830,136 A | 11/1998 | DeLonzor et al. |
| 5,634,459 A | 6/1997 | Gardosi | | 5,830,137 A | 11/1998 | Scharf |
| 5,638,593 A | 6/1997 | Gerhardt et al. | | 5,839,439 A | 11/1998 | Nierlich et al. |
| 5,638,818 A | 6/1997 | Diab et al. | | RE36,000 E | 12/1998 | Swedlow et al. |
| 5,645,060 A | 7/1997 | Yorkey et al. | | 5,842,979 A | 12/1998 | Jarman et al. |

| | | | | | |
|---|---|---|---|---|---|
| 5,842,981 A | 12/1998 | Larsen et al. | 6,064,899 A | 5/2000 | Fein et al. |
| 5,842,982 A | 12/1998 | Mannheimer | 6,067,462 A | 5/2000 | Diab et al. |
| 5,846,190 A | 12/1998 | Woehrle | 6,073,038 A | 6/2000 | Wang et al. |
| 5,851,178 A | 12/1998 | Aronow | 6,078,833 A | 6/2000 | Hueber |
| 5,851,179 A | 12/1998 | Ritson et al. | 6,081,735 A | 6/2000 | Diab et al. |
| 5,853,364 A | 12/1998 | Baker, Jr. et al. | 6,081,742 A | 6/2000 | Amano et al. |
| 5,860,919 A | 1/1999 | Kiani-Azarbayjany et al. | 6,083,157 A | 7/2000 | Noller |
| 5,865,736 A | 2/1999 | Baker, Jr. et al. | 6,083,172 A | 7/2000 | Baker, Jr. et al. |
| 5,871,442 A | 2/1999 | Madarasz et al. | 6,088,607 A | 7/2000 | Diab et al. |
| 5,879,294 A | 3/1999 | Anderson et al. | 6,094,592 A | 7/2000 | Yorkey et al. |
| 5,885,213 A | 3/1999 | Richardson et al. | 6,095,974 A | 8/2000 | Shemwell et al. |
| 5,890,929 A | 4/1999 | Mills et al. | 6,104,938 A | 8/2000 | Huiku et al. |
| 5,891,021 A | 4/1999 | Dillon et al. | 6,112,107 A | 8/2000 | Hannula |
| 5,891,022 A | 4/1999 | Pologe | 6,113,541 A | 9/2000 | Dias et al. |
| 5,891,024 A | 4/1999 | Jarman et al. | 6,115,621 A | 9/2000 | Chin |
| 5,891,025 A | 4/1999 | Buschmann et al. | 6,122,535 A | 9/2000 | Kaestle et al. |
| 5,891,026 A | 4/1999 | Wang et al. | 6,133,994 A | 10/2000 | Mathews et al. |
| 5,902,235 A | 5/1999 | Lewis et al. | 6,135,952 A | 10/2000 | Coetzee |
| 5,910,108 A | 6/1999 | Solenberger | 6,144,444 A | 11/2000 | Haworth et al. |
| 5,911,690 A | 6/1999 | Rall | 6,144,867 A | 11/2000 | Walker et al. |
| 5,912,656 A | 6/1999 | Tham et al. | 6,144,868 A | 11/2000 | Parker |
| 5,913,819 A | 6/1999 | Taylor et al. | 6,149,481 A | 11/2000 | Wang et al. |
| 5,916,154 A | 6/1999 | Hobbs et al. | 6,150,951 A | 11/2000 | Olejniczak |
| 5,916,155 A | 6/1999 | Levinson et al. | 6,151,107 A | 11/2000 | Schöllerman et al. |
| 5,919,133 A | 7/1999 | Taylor et al. | 6,151,518 A | 11/2000 | Hayashi |
| 5,919,134 A | 7/1999 | Diab | 6,152,754 A | 11/2000 | Gerhardt et al. |
| 5,920,263 A | 7/1999 | Huttenhoff et al. | 6,154,667 A | 11/2000 | Miura et al. |
| 5,921,921 A | 7/1999 | Potratz et al. | 6,157,850 A | 12/2000 | Diab et al. |
| 5,922,607 A | 7/1999 | Bernreuter | 6,163,175 A | 12/2000 | Larsen et al. |
| 5,924,979 A | 7/1999 | Swedlow et al. | 6,163,715 A | 12/2000 | Larsen et al. |
| 5,924,980 A | 7/1999 | Coetzee | 6,165,005 A | 12/2000 | Mills et al. |
| 5,924,982 A | 7/1999 | Chin | 6,173,196 B1 | 1/2001 | Delonzor et al. |
| 5,924,985 A | 7/1999 | Jones | 6,178,343 B1 | 1/2001 | Bindszus et al. |
| 5,934,277 A | 8/1999 | Mortz | 6,181,958 B1 | 1/2001 | Steuer et al. |
| 5,934,925 A | 8/1999 | Tobler et al. | 6,181,959 B1 | 1/2001 | Schöllerman et al. |
| 5,940,182 A | 8/1999 | Lepper, Jr. et al. | 6,184,521 B1 | 2/2001 | Coffin, IV et al. |
| 5,954,644 A | 9/1999 | Dettling et al. | 6,188,470 B1 | 2/2001 | Grace |
| 5,960,610 A | 10/1999 | Levinson et al. | 6,192,260 B1 | 2/2001 | Chance |
| 5,961,450 A | 10/1999 | Merchant et al. | 6,195,575 B1 | 2/2001 | Levinson |
| 5,961,452 A | 10/1999 | Chung et al. | 6,198,951 B1 | 3/2001 | Kosuda et al. |
| 5,964,701 A | 10/1999 | Asada et al. | 6,206,830 B1 | 3/2001 | Diab et al. |
| 5,971,930 A | 10/1999 | Elghazzawi | 6,213,952 B1 | 4/2001 | Finarov et al. |
| 5,978,691 A | 11/1999 | Mills | 6,217,523 B1 | 4/2001 | Amano et al. |
| 5,978,693 A | 11/1999 | Hamilton et al. | 6,222,189 B1 | 4/2001 | Misner et al. |
| 5,983,122 A | 11/1999 | Jarman et al. | 6,226,539 B1 | 5/2001 | Potratz |
| 5,987,343 A | 11/1999 | Kinast | 6,226,540 B1 | 5/2001 | Bernreuter |
| 5,991,648 A | 11/1999 | Levin | 6,229,856 B1 | 5/2001 | Diab et al. |
| 5,995,855 A | 11/1999 | Kiani et al. | 6,230,035 B1 | 5/2001 | Aoyagi et al. |
| 5,995,856 A | 11/1999 | Mannheimer et al. | 6,233,470 B1 | 5/2001 | Tsuchiya |
| 5,995,858 A | 11/1999 | Kinast | 6,236,871 B1 | 5/2001 | Tsuchiya |
| 5,995,859 A | 11/1999 | Takahashi | 6,236,872 B1 | 5/2001 | Diab et al. |
| 5,997,343 A | 12/1999 | Mills et al. | 6,240,305 B1 | 5/2001 | Tsuchiya |
| 5,999,834 A | 12/1999 | Wang et al. | 6,253,097 B1 | 6/2001 | Aronow et al. |
| 6,002,952 A | 12/1999 | Diab et al. | 6,253,098 B1 | 6/2001 | Walker et al. |
| 6,005,658 A | 12/1999 | Kaluza et al. | 6,256,523 B1 | 7/2001 | Diab et al. |
| 6,006,120 A | 12/1999 | Levin | 6,256,524 B1 | 7/2001 | Walker et al. |
| 6,011,985 A | 1/2000 | Athan et al. | 6,261,236 B1 | 7/2001 | Grimblatov |
| 6,011,986 A | 1/2000 | Diab et al. | 6,263,221 B1 | 7/2001 | Chance et al. |
| 6,014,576 A | 1/2000 | Raley et al. | 6,263,222 B1 | 7/2001 | Diab et al. |
| 6,018,673 A | 1/2000 | Chin et al. | 6,263,223 B1 | 7/2001 | Shepherd et al. |
| 6,018,674 A | 1/2000 | Aronow | 6,266,546 B1 | 7/2001 | Steuer et al. |
| 6,022,321 A | 2/2000 | Amano et al. | 6,266,547 B1 | 7/2001 | Walker et al. |
| 6,023,541 A | 2/2000 | Merchant et al. | 6,272,363 B1 | 8/2001 | Casciani et al. |
| 6,026,312 A | 2/2000 | Shemwell et al. | 6,278,522 B1 | 8/2001 | Lepper, Jr. et al. |
| 6,026,314 A | 2/2000 | Amerov et al. | 6,280,213 B1 | 8/2001 | Tobler et al. |
| 6,031,603 A | 2/2000 | Fine et al. | 6,280,381 B1 | 8/2001 | Malin et al. |
| 6,035,223 A | 3/2000 | Baker, Jr. | 6,285,894 B1 | 9/2001 | Oppelt et al. |
| 6,036,642 A | 3/2000 | Diab et al. | 6,285,895 B1 | 9/2001 | Ristolainen et al. |
| 6,041,247 A | 3/2000 | Weckstrom et al. | 6,285,896 B1 | 9/2001 | Tobler et al. |
| 6,044,283 A | 3/2000 | Fein et al. | 6,298,252 B1 | 10/2001 | Kovach et al. |
| 6,047,201 A | 4/2000 | Jackson, III | 6,308,089 B1 | 10/2001 | Von der Ruhr et al. |
| 6,061,584 A | 5/2000 | Lovejoy et al. | 6,321,100 B1 | 11/2001 | Parker |
| 6,064,898 A | 5/2000 | Aldrich | 6,330,468 B1 | 12/2001 | Scharf |

| | | | | | | |
|---|---|---|---|---|---|---|
| 6,334,065 B1 | 12/2001 | Al-Ali et al. | | 6,553,241 B2 | 4/2003 | Mannheimer et al. |
| 6,339,715 B1 | 1/2002 | Bahr et al. | | 6,553,242 B2 | 4/2003 | Sarussi |
| 6,343,223 B1 | 1/2002 | Chin et al. | | 6,553,243 B2 | 4/2003 | Gurley |
| 6,343,224 B1 | 1/2002 | Parker | | 6,556,852 B1 | 4/2003 | Schulze et al. |
| 6,349,228 B1 | 2/2002 | Kiani et al. | | 6,560,470 B1 | 5/2003 | Pologe |
| 6,351,658 B1 | 2/2002 | Middleman et al. | | 6,564,077 B2 | 5/2003 | Mortara |
| 6,353,750 B1 | 3/2002 | Kimura et al. | | 6,571,113 B1 | 5/2003 | Fein et al. |
| 6,356,774 B1 | 3/2002 | Bernstein et al. | | 6,571,114 B1 | 5/2003 | Koike et al. |
| 6,360,113 B1 | 3/2002 | Dettling | | 6,574,491 B2 | 6/2003 | Elghazzawi |
| 6,360,114 B1 | 3/2002 | Diab et al. | | 6,580,086 B1 | 6/2003 | Schulz et al. |
| 6,361,501 B1 | 3/2002 | Amano et al. | | 6,584,336 B1 | 6/2003 | Ali et al. |
| 6,363,269 B1 | 3/2002 | Hanna et al. | | 6,587,703 B2 | 7/2003 | Cheng et al. |
| 6,364,675 B1 * | 4/2002 | Brauer et al. ............... 439/159 | | 6,587,704 B1 | 7/2003 | Fine et al. |
| 6,370,408 B1 | 4/2002 | Merchant et al. | | 6,589,172 B2 | 7/2003 | Williams et al. |
| 6,370,409 B1 | 4/2002 | Chung et al. | | 6,591,122 B2 | 7/2003 | Schmitt |
| 6,374,129 B1 | 4/2002 | Chin et al. | | 6,591,123 B2 | 7/2003 | Fein et al. |
| 6,377,829 B1 | 4/2002 | Al-Ali et al. | | 6,594,511 B2 | 7/2003 | Stone et al. |
| 6,381,479 B1 | 4/2002 | Norris | | 6,594,512 B2 | 7/2003 | Huang |
| 6,381,480 B1 | 4/2002 | Stoddart et al. | | 6,594,513 B1 | 7/2003 | Jobsis et al. |
| 6,385,471 B1 | 5/2002 | Mortz | | 6,597,931 B1 | 7/2003 | Cheng et al. |
| 6,385,821 B1 | 5/2002 | Modgil et al. | | 6,597,933 B2 | 7/2003 | Kiani et al. |
| 6,388,240 B2 | 5/2002 | Schulz et al. | | 6,600,940 B1 | 7/2003 | Fein et al. |
| 6,393,310 B1 | 5/2002 | Kuenster | | 6,606,510 B2 | 8/2003 | Swedlow et al. |
| 6,397,091 B2 | 5/2002 | Diab et al. | | 6,606,511 B1 | 8/2003 | Ali et al. |
| 6,397,092 B1 | 5/2002 | Norris et al. | | 6,606,512 B2 | 8/2003 | Muz et al. |
| 6,397,093 B1 | 5/2002 | Aldrich | | 6,615,064 B1 | 9/2003 | Aldrich |
| 6,400,971 B1 | 6/2002 | Finarov et al. | | 6,615,065 B1 | 9/2003 | Barrett et al. |
| 6,400,972 B1 | 6/2002 | Fine | | 6,618,602 B2 | 9/2003 | Levin |
| 6,402,690 B1 | 6/2002 | Rhee et al. | | 6,622,034 B1 | 9/2003 | Gorski et al. |
| 6,408,198 B1 | 6/2002 | Hanna et al. | | 6,628,975 B1 | 9/2003 | Fein et al. |
| 6,411,832 B1 | 6/2002 | Guthermann | | 6,631,281 B1 | 10/2003 | Kästle |
| 6,411,833 B1 | 6/2002 | Baker, Jr. et al. | | 6,643,530 B2 | 11/2003 | Diab et al. |
| 6,419,671 B1 | 7/2002 | Lemberg | | 6,643,531 B1 | 11/2003 | Katarow |
| 6,421,549 B1 | 7/2002 | Jacques | | 6,647,279 B2 | 11/2003 | Pologe |
| 6,430,423 B2 | 8/2002 | DeLonzor et al. | | 6,647,280 B2 | 11/2003 | Bahr et al. |
| 6,430,513 B1 | 8/2002 | Wang et al. | | 6,650,917 B2 | 11/2003 | Diab et al. |
| 6,430,525 B1 | 8/2002 | Weber et al. | | 6,650,918 B2 | 11/2003 | Terry |
| 6,434,408 B1 | 8/2002 | Heckel et al. | | 6,654,621 B2 | 11/2003 | Palatnik et al. |
| 6,438,399 B1 | 8/2002 | Kurth | | 6,654,622 B1 | 11/2003 | Eberhard et al. |
| 6,449,501 B1 | 9/2002 | Reuss | | 6,654,623 B1 | 11/2003 | Kästle |
| 6,453,183 B1 | 9/2002 | Walker | | 6,654,624 B2 | 11/2003 | Diab et al. |
| 6,453,184 B1 | 9/2002 | Hyogo et al. | | 6,658,276 B2 | 12/2003 | Kianl et al. |
| 6,456,862 B2 | 9/2002 | Benni | | 6,658,277 B2 | 12/2003 | Wasserman |
| 6,461,305 B1 | 10/2002 | Schnall | | 6,662,033 B2 | 12/2003 | Casciani et al. |
| 6,463,310 B1 | 10/2002 | Swedlow et al. | | 6,665,551 B1 | 12/2003 | Suzuki |
| 6,463,311 B1 | 10/2002 | Diab | | 6,668,182 B2 | 12/2003 | Hubelbank |
| 6,466,808 B1 | 10/2002 | Chin et al. | | 6,668,183 B2 | 12/2003 | Hicks et al. |
| 6,466,809 B1 | 10/2002 | Riley | | 6,671,526 B1 | 12/2003 | Aoyagi et al. |
| 6,470,199 B1 | 10/2002 | Kopotic et al. | | 6,671,528 B2 | 12/2003 | Steuer et al. |
| 6,470,200 B2 | 10/2002 | Walker et al. | | 6,671,530 B2 | 12/2003 | Chung et al. |
| 6,480,729 B2 | 11/2002 | Stone | | 6,671,531 B2 | 12/2003 | Al-Ali et al. |
| 6,490,466 B1 | 12/2002 | Fein et al. | | 6,671,532 B1 | 12/2003 | Fudge et al. |
| 6,496,711 B1 | 12/2002 | Athan et al. | | 6,675,031 B1 | 1/2004 | Porges et al. |
| 6,498,942 B1 | 12/2002 | Esenaliev et al. | | 6,678,543 B2 | 1/2004 | Diab et al. |
| 6,501,974 B2 | 12/2002 | Huiku | | 6,681,126 B2 | 1/2004 | Solenberger |
| 6,501,975 B2 | 12/2002 | Diab et al. | | 6,681,128 B2 | 1/2004 | Steuer et al. |
| 6,505,060 B1 | 1/2003 | Norris | | 6,681,454 B2 | 1/2004 | Modgil et al. |
| 6,505,061 B2 | 1/2003 | Larson | | 6,684,090 B2 | 1/2004 | Ali et al. |
| 6,505,133 B1 | 1/2003 | Hanna et al. | | 6,684,091 B2 | 1/2004 | Parker |
| 6,510,329 B2 | 1/2003 | Heckel | | 6,694,160 B2 | 2/2004 | Chin |
| 6,510,331 B1 | 1/2003 | Williams et al. | | 6,697,653 B2 | 2/2004 | Hanna |
| 6,512,937 B2 | 1/2003 | Blank et al. | | 6,697,655 B2 | 2/2004 | Sueppel et al. |
| 6,515,273 B2 | 2/2003 | Al-Ali | | 6,697,656 B1 | 2/2004 | Al-Ali |
| 6,519,484 B1 | 2/2003 | Lovejoy et al. | | 6,697,658 B2 | 2/2004 | Al-Ali |
| 6,519,486 B1 | 2/2003 | Edgar, Jr. et al. | | RE38,476 E | 3/2004 | Diab et al. |
| 6,519,487 B1 | 2/2003 | Parker | | 6,699,194 B1 | 3/2004 | Diab et al. |
| 6,525,386 B1 | 2/2003 | Mills et al. | | 6,699,199 B2 | 3/2004 | Asada et al. |
| 6,526,300 B1 | 2/2003 | Kiani et al. | | 6,701,170 B2 | 3/2004 | Stetson |
| 6,526,301 B2 | 2/2003 | Larsen et al. | | 6,702,752 B2 | 3/2004 | Dekker |
| 6,564,088 B1 | 3/2003 | Soller et al. | | 6,707,257 B2 | 3/2004 | Norris |
| 6,541,756 B2 | 4/2003 | Schulz et al. | | 6,708,049 B1 | 3/2004 | Berson et al. |
| 6,542,764 B1 | 4/2003 | Al-Ali et al. | | 6,709,402 B2 | 3/2004 | Dekker |
| 6,546,267 B1 | 4/2003 | Sugiura et al. | | 6,711,424 B1 | 3/2004 | Fine et al. |

| Patent | Date | Name |
|---|---|---|
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 7,024,235 B2 | 11/2004 | Melker et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,117,590 B2 | 10/2006 | Koenig et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,371,981 B2 * | 5/2008 | Abdul-Hafiz ............ 200/51 R |
| 7,377,794 B2 | 5/2008 | Al-Ali et al. |
| 7,427,165 B2 | 9/2008 | Benaron et al. |
| 7,435,112 B1 * | 10/2008 | Miller et al. ............. 439/141 |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |

| | | | | | | |
|---|---|---|---|---|---|---|
| 2002/0038078 A1 | 3/2002 | Ito | | 2004/0204636 A1 | 10/2004 | Diab et al. |
| 2002/0042558 A1 | 4/2002 | Mendelson | | 2004/0204637 A1 | 10/2004 | Diab et al. |
| 2002/0068859 A1 | 6/2002 | Knopp | | 2004/0204638 A1 | 10/2004 | Diab et al. |
| 2002/0128544 A1 | 9/2002 | Diab et al. | | 2004/0204639 A1 | 10/2004 | Casciani et al. |
| 2002/0133067 A1 | 9/2002 | Jackson, III | | 2004/0204865 A1 | 10/2004 | Lee et al. |
| 2002/0156354 A1 | 10/2002 | Larson | | 2004/0210146 A1 | 10/2004 | Diab et al. |
| 2002/0173706 A1 | 11/2002 | Takatani | | 2004/0215069 A1 | 10/2004 | Mannheimer |
| 2002/0173709 A1 | 11/2002 | Fine et al. | | 2004/0230107 A1 | 11/2004 | Asada et al. |
| 2002/0190863 A1 | 12/2002 | Lynn | | 2004/0230108 A1 | 11/2004 | Melker et al. |
| 2002/0198442 A1 | 12/2002 | Rantala et al. | | 2004/0236196 A1 | 11/2004 | Diab et al. |
| 2003/0018243 A1 | 1/2003 | Gerhardt et al. | | 2004/0242980 A1 | 12/2004 | Kiani et al. |
| 2003/0036690 A1 | 2/2003 | Geddes et al. | | 2004/0249252 A1 | 12/2004 | Fine et al. |
| 2003/0045785 A1 | 3/2003 | Diab et al. | | 2004/0257557 A1 | 12/2004 | Block et al. |
| 2003/0073889 A1 | 4/2003 | Keilbach et al. | | 2004/0260161 A1 | 12/2004 | Melker et al. |
| 2003/0073890 A1 | 4/2003 | Hanna | | 2004/0267103 A1 | 12/2004 | Li et al. |
| 2003/0100840 A1 | 5/2003 | Sugiura et al. | | 2004/0267104 A1 | 12/2004 | Hannula et al. |
| 2003/0132495 A1 | 7/2003 | Mills et al. | | 2004/0267140 A1 | 12/2004 | Ito et al. |
| 2003/0135099 A1 | 7/2003 | Al-Ali | | 2005/0004479 A1 | 1/2005 | Townsend et al. |
| 2003/0162414 A1 | 8/2003 | Schulz et al. | | 2005/0010092 A1 | 1/2005 | Weber et al. |
| 2003/0171662 A1 | 9/2003 | O'Connor et al. | | 2005/0020887 A1 | 1/2005 | Goldberg |
| 2003/0176776 A1 | 9/2003 | Huiku | | 2005/0020894 A1 | 1/2005 | Norris et al. |
| 2003/0181799 A1 | 9/2003 | Lindekugel et al. | | 2005/0033128 A1 | 2/2005 | Ali et al. |
| 2003/0187337 A1 | 10/2003 | Tarassenko et al. | | 2005/0033129 A1 | 2/2005 | Edgar, Jr. et al. |
| 2003/0195402 A1 | 10/2003 | Fein et al. | | 2005/0043599 A1 | 2/2005 | O'Mara |
| 2003/0197679 A1 | 10/2003 | Ali et al. | | 2005/0043600 A1 | 2/2005 | Diab et al. |
| 2003/0212316 A1 | 11/2003 | Leiden et al. | | 2005/0049470 A1 | 3/2005 | Terry |
| 2003/0225323 A1 | 12/2003 | Kiani et al. | | 2005/0049471 A1 | 3/2005 | Aceti |
| 2003/0225337 A1 | 12/2003 | Scharf et al. | | 2005/0075550 A1 | 4/2005 | Lindekugel |
| 2003/0236452 A1 | 12/2003 | Melker et al. | | 2005/0177034 A1 | 8/2005 | Beaumont |
| 2003/0236647 A1 | 12/2003 | Yoon et al. | | 2005/0197548 A1 | 9/2005 | Dietiker |
| 2004/0006261 A1 | 1/2004 | Swedlow et al. | | 2005/0228248 A1 | 10/2005 | Dietiker |
| 2004/0010188 A1 | 1/2004 | Wasserman et al. | | 2005/0277819 A1 | 12/2005 | Kiani et al. |
| 2004/0024297 A1 | 2/2004 | Chen et al. | | 2005/0283059 A1 | 12/2005 | Iyer et al. |
| 2004/0024326 A1 | 2/2004 | Yeo et al. | | 2006/0058594 A1 | 3/2006 | Ishizuka et al. |
| 2004/0034293 A1 | 2/2004 | Kimball | | 2006/0084852 A1 | 4/2006 | Mason et al. |
| 2004/0039272 A1 | 2/2004 | Abdul-Hafiz et al. | | 2006/0089547 A1 | 4/2006 | Sarussi |
| 2004/0039273 A1 | 2/2004 | Terry | | 2006/0106294 A1 | 5/2006 | Maser et al. |
| 2004/0054269 A1 | 3/2004 | Rantala et al. | | 2006/0195028 A1 | 8/2006 | Hannula et al. |
| 2004/0054291 A1 | 3/2004 | Schulz et al. | | 2006/0224058 A1 | 10/2006 | Mannheimer |
| 2004/0059209 A1 | 3/2004 | Al-Ali et al. | | 2006/0241363 A1 | 10/2006 | Al-Ali et al. |
| 2004/0059210 A1 | 3/2004 | Stetson | | 2006/0247501 A1 | 11/2006 | Ali |
| 2004/0064020 A1 | 4/2004 | Diab et al. | | 2006/0258921 A1 | 12/2006 | Addison et al. |
| 2004/0068164 A1 | 4/2004 | Diab et al. | | 2007/0032710 A1 | 2/2007 | Raridan et al. |
| 2004/0087846 A1 | 5/2004 | Wasserman | | 2007/0032712 A1 | 2/2007 | Raridan et al. |
| 2004/0092805 A1 | 5/2004 | Yarita | | 2007/0032715 A1 | 2/2007 | Eghbal et al. |
| 2004/0097797 A1 | 5/2004 | Porges et al. | | 2007/0073126 A1 | 3/2007 | Raridan, Jr. |
| 2004/0098009 A1 | 5/2004 | Boecker et al. | | 2008/0071153 A1 | 3/2008 | Al-Ali et al. |
| 2004/0107065 A1 | 6/2004 | Al-Ali et al. | | 2008/0081954 A1 | 4/2008 | Meyer et al. |
| 2004/0116788 A1 | 6/2004 | Chernoguz et al. | | 2008/0220633 A1 | 9/2008 | Al-Ali et al. |
| 2004/0116789 A1 | 6/2004 | Boaz et al. | | 2008/0255435 A1 | 10/2008 | Al-Ali et al. |
| 2004/0117891 A1 | 6/2004 | Hannula et al. | | | | |
| 2004/0122300 A1 | 6/2004 | Boas et al. | | | FOREIGN PATENT DOCUMENTS | |
| 2004/0122302 A1 | 6/2004 | Mason et al. | | | | |
| 2004/0133087 A1 | 7/2004 | Ali et al. | | DE | 19632361 | 2/1997 |
| 2004/0133088 A1 | 7/2004 | Al-Ali et al. | | EP | 0127947 | 12/1984 |
| 2004/0138538 A1 | 7/2004 | Stetson | | EP | 0204259 | 12/1986 |
| 2004/0138540 A1 | 7/2004 | Baker, Jr. et al. | | EP | 0352923 | 1/1990 |
| 2004/0143172 A1 | 7/2004 | Fudge et al. | | EP | 0724860 | 8/1996 |
| 2004/0147821 A1 | 7/2004 | Al-Ali et al. | | FR | 2685865 | 1/1992 |
| 2004/0147822 A1 | 7/2004 | Al-Ali et al. | | JP | 2111343 | 4/1990 |
| 2004/0147823 A1 | 7/2004 | Kiani et al. | | JP | 5049625 | 3/1993 |
| 2004/0147824 A1 | 7/2004 | Diab et al. | | JP | 6014906 | 1/1994 |
| 2004/0152965 A1 | 8/2004 | Diab et al. | | JP | 6269430 | 9/1994 |
| 2004/0158134 A1 | 8/2004 | Diab et al. | | JP | 7001273 | 1/1995 |
| 2004/0158135 A1 | 8/2004 | Baker, Jr. et al. | | JP | 7236625 | 9/1995 |
| 2004/0162472 A1 | 8/2004 | Berson et al. | | JP | 2000237170 | 9/2000 |
| 2004/0171920 A1 | 9/2004 | Mannheimer et al. | | JP | 3116259 | 10/2000 |
| 2004/0171948 A1 | 9/2004 | Terry | | JP | 3116260 | 10/2000 |
| 2004/0176671 A1 | 9/2004 | Fine et al. | | JP | 2003275192 | 9/2003 |
| 2004/0181133 A1 | 9/2004 | Al-Ali et al. | | JP | 2004089546 | 3/2004 |
| 2004/0181134 A1 | 9/2004 | Baker, Jr. et al. | | JP | 2004329406 | 11/2004 |
| 2004/0186358 A1 | 9/2004 | Chernow et al. | | JP | 2004337605 | 12/2004 |
| 2004/0199063 A1 | 10/2004 | O'Neil et al. | | JP | 2004344367 | 12/2004 |

| | | |
|---|---|---|
| JP | 2004351107 | 12/2004 |
| WO | WO8909566 | 10/1989 |
| WO | WO9001293 | 2/1990 |
| WO | WO9111137 | 8/1991 |
| WO | WO93/16629 | 9/1993 |
| WO | WO9502358 | 1/1995 |
| WO | WO9736536 | 10/1997 |
| WO | WO98/57577 | 12/1998 |
| WO | WO9947039 | 9/1999 |
| WO | WO0059374 | 10/2000 |
| WO | WO03011127 | 2/2003 |
| WO | WO2005010567 | 2/2005 |
| WO | WO2005010568 | 3/2005 |

OTHER PUBLICATIONS

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Dekock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Design and Analysis," *Proceedings of the 22nd Annual EMBS International Conference*, Chicago, Illinois; Jul. 23-28, 2000; pp. 27926-2799.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Urquhart, C., et al.; "Ear probe pulse oximeters and neonates," *Anaesthesia*, vol. 60, p. 294 (2005).

\* cited by examiner

SINGLE USE CONNECTOR FOR PULSE OXIMETRY SENSORS

BACKGROUND

In medicine, a plethysmograph is an instrument that measures physiological parameters, such as variations in the size of an organ or body part, through an analysis of the blood passing through or present in the targeted body part, or a depiction of these variations. An oximeter is an instrument that determines the oxygen saturation of the blood. One common type of oximeter is a pulse oximeter, which determines oxygen saturation by analysis of an optically sensed plethysmograph.

A pulse oximeter is a medical device that indirectly measures the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient.

A pulse oximeter may include a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth". From the waveform of the PPG, it is possible to identify the pulse rate of the patient and when each individual pulse occurs. In addition, by comparing the intensities of two wavelengths at different points in the pulse cycle, it is possible to estimate the blood oxygen saturation of hemoglobin in arterial blood. This relies on the observation that highly oxygenated blood will absorb relatively less red light and more infrared light than blood with lower oxygen saturation.

Many $SpO_2$ sensors are constructed with a male connector having pins molded in plastic into a shape that can be fitted into a complementary female connector constructed with openings for receiving the pins from the male connector. The female connector socket is typically located on the main housing of the oximeter. The standard RS 232 connector is one common type of connector used.

As with many medical devices, $SpO_2$ sensors are designed for single patient use in order to prevent the spread of disease between patients as well as to ensure that the sensor will operate to the exacting specifications of a medical device. However, whether unwittingly or not, it is not uncommon for oximetry sensors to be reused for different patients. Regardless of the reason, this reuse is not desirable.

SUMMARY

This disclosure describes systems and methods for a SpO2 sensor that is limited to a single use through the use of a single-use connector on the sensor assembly. As discussed in greater detail below, this disclosure describes a sensor which consists of a single-use male connector for use with female connector on the oximeter. The connector includes a housing enclosing one or more pins, one or more movable members, and a locking mechanism. Upon engagement of the male connector with the female connector the locking mechanism activates such that when the female connector is removed, the moveable member moves from a first position to a second position and locks into the second position. When in the second position the male connector can not engage the female connector, thereby limiting the male connector to a single use engagement.

In one aspect, the disclosure describes a single-use male connector for use with female connector. The male connector includes a housing enclosing one or more pins, one or more movable members adjacent to the other one or more pins and a locking mechanism. When engaged with the female connector, the engagement activates the locking mechanism such that when the female connector is removed, the moveable member moves from a first position to a second position and locks into the second position. The second position is such that the male connector can not engage the female connector, thereby limiting the male connector to a single use. In the single-use male connector, one or more of the pins may penetrate the movable member.

In another aspect, the disclosure describes a single-use oximetry sensor that includes: a sensor including at least one light source and at least one light detector; and a single-use connector electrically connected to the sensor via a cable containing one or more wires. The single-use connector is adapted for use with a complementary connector on an oximeter. The single-use connector contains a movable member that, upon disengagement after a first engagement with the complementary female, moves to a position preventing further engagement with the complementary female connector.

In a further aspect, the single-use oximetry sensor is provided with a single-use male connector for use with a complementary female connector. The single-use male connector may further include: a housing enclosing one or more pins, one or more movable members adjacent to the other one or more pins; and a locking mechanism. Engagement of the single-use male connector into the complementary female connector activates the locking mechanism such that when the female connector is removed, the moveable member moves from a first position to a second position and locks into the second position. When in the second position the male connector can not engage the female connector, thereby limiting the male connector to a single use engagement.

The single-use connector may further be designed so that some or all of the one or more pins penetrate the movable member. The single-use connector may further be designed so that when the single-use male connector is engaged the movable member moves from a third position to a first position. The single-use connector may further be designed so that the movable member is penetrated by no pins. The single-use connector may further be designed so that the movable member is moved from the first position to the second position via a spring force exerted by a spring mechanism. The single-use connector may further be designed so that the spring mechanism is between the movable member and a back face of the housing. The single-use connector may further be designed so that the spring mechanism is integral with the locking mechanism. The single-use connector may further be designed so that the integral spring and locking mechanism is between the movable member and a back face of the housing. The single-use connector may further be designed so that the locking mechanism is between the movable member and a back face of the housing. The single-use connector may further be designed so that the housing is constructed to prevent a user from unlocking the movable member from the second position, thereby preventing a user from reusing the sensor after a first use.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices and sensors, the present disclosure will discuss the implementation of these techniques in a pulse oximeter. The reader will understand that the technology described in the context of a pulse oximeter could be adapted for use with other systems that utilize sensors attached to the body such as electrocardiographs and electroencephalographs.

Figure 1:
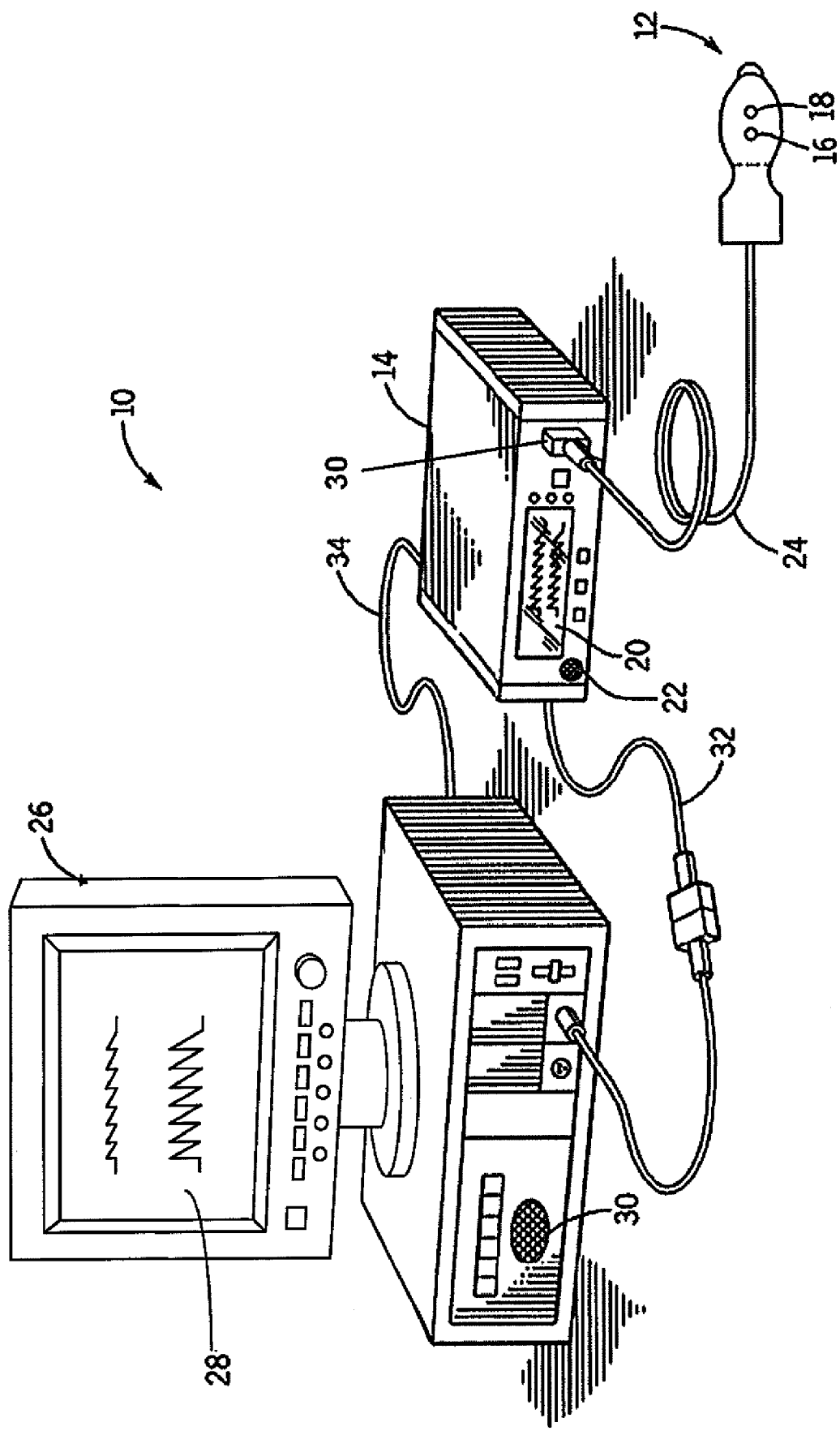
FIG. 1 is a perspective view of the single-use connector and sensor system.

FIG. 1 is a perspective view of an embodiment of a pulse oximetry system 10. The system 10 includes a sensor 12 and a pulse oximetry monitor 14. The sensor 12 includes an emitter 16 for emitting light at one or more wavelengths into a patient's tissue. A detector 18 is also provided in the sensor 12 for detecting the light originally from the emitter 16 that emanates from the patient's tissue after passing through the tissue. The emitter 16 and detector 18 may be on opposite sides of a digit such as a finger or toe, in which case the light that is emanating from the tissue has passed completely through the digit. In an alternative embodiment, the emitter 16 and detector 18 may be arranged so that light from the emitter 16 penetrates the tissue and is reflected by the tissue into the detector 18, such as a sensor designed to obtain pulse oximetry data from a patient's forehead.

The sensor 12 may be connected to and draw its power from the monitor 14 as shown. The sensor is connected to the monitor by a single-use SpO$_2$ connector. The monitor 14 may be configured to calculate physiological parameters based on data received from the sensor 12 relating to light emission and detection. Further, the monitor 14 includes a display 20 configured to display the physiological parameters, other information about the system, and/or alarm indications. In the embodiment shown, the monitor 14 also includes a speaker 22 to provide an audible alarm in the event that the patient's physiological parameters are not within a normal range, as defined based on patient characteristics. The sensor 12 is communicatively coupled to the monitor 14 via a cable 24 and male single-use connector 30. The single-use connector 30 of the sensor 12 is shown engaged with a complimentary connector (not visible) on the monitor 14.

In the illustrated embodiment, the pulse oximetry system 10 also includes a multi-parameter patient monitor 26. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display a patient's oxygen saturation reading generated by the pulse oximetry monitor 14 (referred to as an "SpO$_2$" reading), pulse rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient's physiological characteristics are found to be outside of the normal range. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2A:
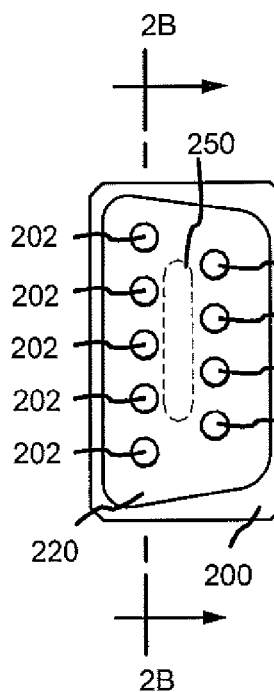
FIG. 2A illustrates a plan view of an embodiment of a single-use connector.

FIG. 2A illustrates a plan view of an embodiment of a single-use connector adapted for use with an oximeter sensor. In the embodiment shown, the male connector 299 takes a form similar to that of an RS 232 connector and includes: a housing 200; the housing 200 enclosing a back face 201; a movable member (in the form of a moveable faceplate 220); one or more pins (in the embodiment shown there are seven pins 202) penetrating holes 222 in the movable member 220; a cable 253; a spring mechanism 250 and a locking mechanism 252 illustrated as one or more latches 255 (illustrated in an exaggerated size in FIG. 2B)) designed to lock the movable member 220 into a use-preventing position 213.

The connector housing 200 can be made of plastic, metal or any suitable material. In addition to the elements shown in FIG. 2A, the housing 200 also includes the electrical wiring which carries the electrical signals from the pins 202 through the cable 253 to the sensor. In an embodiment, the housing 200 is of a unitary construction or otherwise made in such a way as to prevent the connector 299 from being disassembled. Such tamper-proof design prevents the connector 299 from being disassembled in order to reset the movable member after it has been used. In an embodiment, the housing 200 may be constructed so that an attempt to reset the movable member 220 or prevent it from locking after a use will result in the destruction of the housing 200.

The back face 201 can be made of plastic, metal or any other suitable material. The back face 201 is part of the housing 200. The one or more pins 202 are mounted to the back face 201 in a complementary configuration to that of the intended female connector 290 (see FIG. 2C) on the oximeter.

Figure 2B:
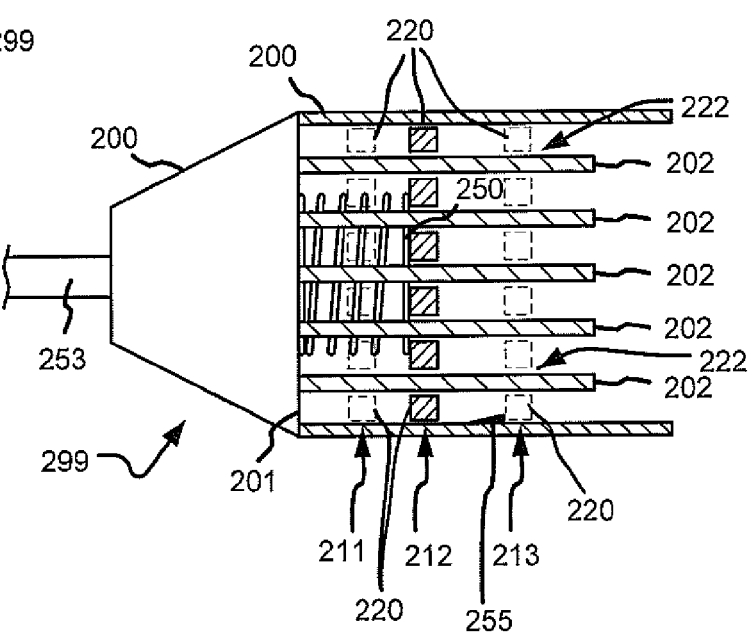
FIG. 2B illustrates a sectional view of the connector in FIG. 2A illustrating the three positions of the movable member relative to the housing.

The connector 299 includes a movable member 220 that is adapted to move between various positions when engaged and disengaged with a complementary connector 290. FIG. 2B illustrates a sectional view of the connector in FIG. 2A illustrating the three positions of the movable member relative to the housing. In the embodiment shown, the moveable member moves from an initial position 212 to an engaged position 211 when engaged with the complementary connector 290. Upon disengagement with the complementary connector 290 the movable member 220 moves from the engaged position 211 to a use-preventing position 213, in which position it is locked in place. In the use-preventing position 213 the movable member 220 is i such a position relative to the pins 202 and the housing 200 that it can no longer be used to engage and or electrically couple to the complementary connector 290. In this position 213, the male connector 299 may be so configured as to not be able to physically engage the female connector 290. Alternatively, while a physical engagement may be possible when in the use-preventing position 213, an electrical engagement may be prevented by limiting the depth to which the pins penetrate the receiving sockets in the female connector 290.

In the embodiment shown in FIGS. 2A and 2B, the movable member takes the form of a face that is substantially the same shape as the back face 201. The movable member 220 moves parallel to the back face 201, within the housing 200. The movable member 220 is penetrated by apertures or holes 222 through which the pins 202 penetrate.

In the embodiment shown, the spring mechanism 250 is mounted to a portion of the back face 201 and operates to provide a spring tension on the movable member 220. In the embodiment shown, the spring mechanism 250 is activated upon engagement of the male connector 299 with the complimentary connector 290. In an alternative embodiment, the spring mechanism 250 may be activated by a different action, e.g., by the act of removing/disengaging the male and female connectors. Regardless, upon disengagement of the male connector 299 from the female connector 290, the spring mechanism 250 operates to force the movable member 220 from the engaged position 211 to the use-preventing position 213. The spring mechanism 250 may include one or more springs of any type or configuration. For example, a coil spring, leaf spring or elastomeric bumper may be used to provide the spring tension. In an embodiment, the spring mechanism 250 may include a release mechanism (not illustrated) so that the spring force is not released until such a time as the moveable member 220 is moved to the engaged position 211 or, alternatively, until such time as the male connector 299 is removed from the female connector 290. Spring tensioning and the contingent release of spring forces in a mechanical device are well known in the mechanical arts and one of skill in the art could identify many different methods and means for achieving the movement of the movable member 220 as described herein.

As described above, the movable member 220 locks in place in the use-preventing position 213 after disengagement from the complementary connector 290. In the embodiment shown, the locking is achieved through the use of one or more latches 255. The latches 255 may be active members or passive contours that allow the movable member to pass in only one direction. In an alternative embodiment, a locking mechanism may be combined with or incorporated into the spring mechanism 250 to prevent the movable member 220 from moving out of the use-preventing position 213 after disengagement of the connectors 299, 290.

As well known in the art the pins 202 can be made in any manner and of any material suitable for creating an electrical contact with the socket it is intended to engage with. In the embodiment shown, the pins 202 may be mounted to the back face 201. The pins 202 are positions so as to align with a female connector socket 290 attached to an oximeter. As described above, the pins 202 are electrically connected by wiring which carries an electrical signal from the pins 202 to the SpO$_2$ sensor. The cable 253 encloses the electrical wiring in a protective, non-conductive coating.

Figure 2C:
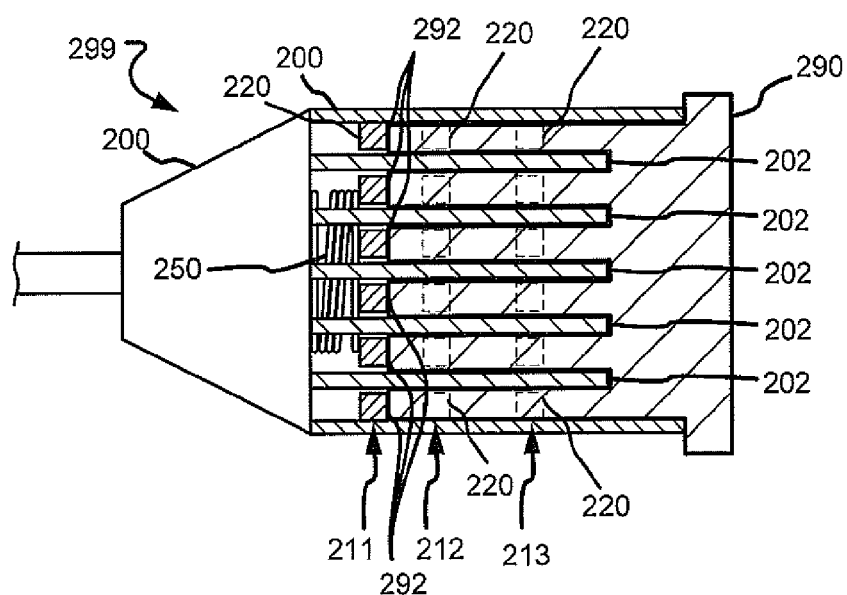
FIG. 2C illustrates a sectional view of the connector of FIGS. 2A and 2B when engaged with a female connector.

FIG. 2C illustrates a sectional view of an embodiment of the engagement of the male connector 299 and female connector 290. Engagement of the male connector 299 into the female connector 290 activates the spring mechanism 250 and locking mechanism 252 such that when the female connector 290 is removed, the moveable member 220 moves from a first, engaged position 211 to a second, use-prevention position 213 and locks into the second position 213. As discussed above, when in the second position 213 the male connector 299 can not engage the female connector 290, thereby limiting the connector to a single-use engagement.

FIG. 2C illustrates the displacement of the movable member 220 from a third, initial position 212 into the first, engaged position 211. In the embodiment shown, this displacement is caused by the force exerted when an operator engages the connectors 299, 290 at which time a forward face 292 of the female connector 290 presses against the movable member 220.

Figure 3:
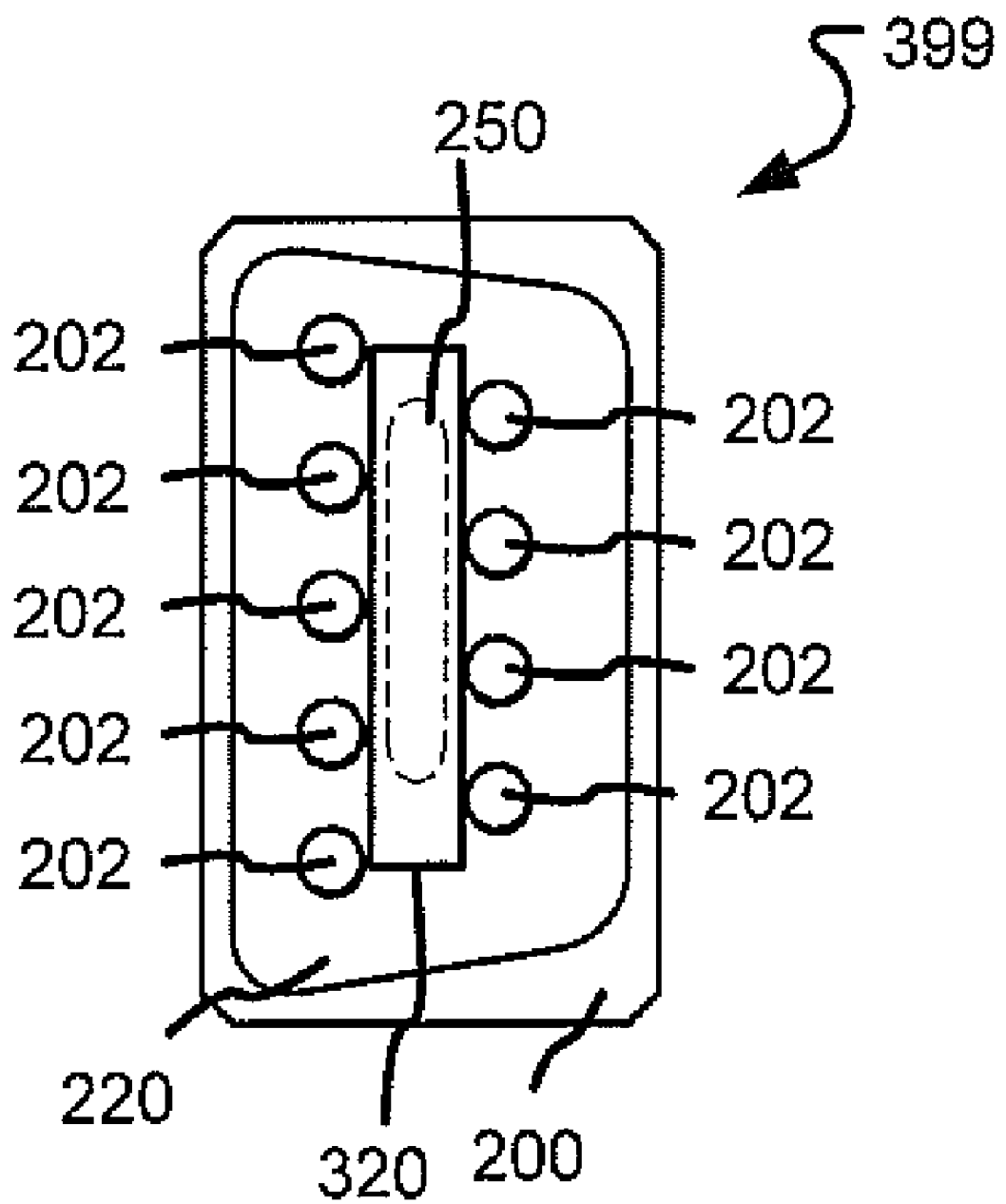
FIG. 3 illustrates an embodiment of a movable member penetrated by no pins.

FIG. 3 illustrates a plan view of a different embodiment of a single-use connector adapted for use with an oximeter sensor. In the embodiment shown, the male connector 299. In the embodiment shown, the movable member 320 is only a portion of a fixed forward face 220 from which the pins 202 extend. In the embodiment shown, the movable member 320 is located within the pins 202 and is not penetrated by any of the pins 202. The movable member 320 operates as described above with respect to FIGS. 2A-2C, i.e., engagement of the connector 399 with a female connector 290 results in the movable member 320 being displaced from an initial position 212 into an engaged position 211. Upon disengagement of the male connector 299 from the female connector 290, the spring mechanism 250 operates to force the movable member 320 from the engaged position 211 to the use-preventing position 213 where it is locked in place by the locking mechanism 252.

Other embodiments in which the shape and extent of the movable member 320 relative to the connector face 220 are also possible. Any such shape, whether penetrated by pins 202 or not, may be used to prevent the connector from being used after a single use.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components and individual functions implemented in different manners and with different elements in order to achieve the same results. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. For example, multiple movable faces may be used in a single connector. Additionally, the use-prevention position of the movable member may be any position that prevents effective reconnection with the complementary connector including a position in which the pins are entirely enclosed by the housing and movable member or in which the moveable member extends out from the housing. Alternatively, any suitable locking mechanism and/or spring mechanism may be used to achieve the result of moving a member to prevent use after a first use.

Numerous other changes may be made which will readily suggest themselves to those skilled in the art and which are encompassed in the spirit of the disclosure and as defined in the appended claims.

What is claimed is:

1. A single-use connector for use with a complementary connector comprising:
   a housing enclosing a pin, a movable member adjacent to the pin and a locking mechanism;
   wherein engagement of the single-use connector into the complementary connector moves the moveable member from an initial position to an engaged position and activates the locking mechanism such that when the complementary connector is removed, the moveable member moves from the engaged position, past the initial position and to a use-preventing position and locks into the use-preventing position; and
   wherein when in the use-preventing position the single-use connector cannot engage the complementary connector.

2. The connector of claim 1, wherein the pin penetrates the movable member.

3. The connector of claim 1, wherein the movable member is not penetrated by the pin.

4. A single-use oximetry sensor comprising:
   a sensor comprising a light source and a light detector; and
   a single-use connector electrically connected to the sensor via a cable comprising one or more wires;
   wherein the single-use connector comprises:
      a movable member that, upon disengagement from a complementary connector, moves to a use-preventing position preventing further engagement with the complementary connector.

5. The single-use oximetry sensor of claim 4 wherein the single-use connector comprises:
   a housing enclosing a pin wherein the movable member is adjacent to the pin; and
   a locking mechanism;
   wherein engagement of the single-use connector into the complementary connector activates the locking mechanism such that when the complementary connector is removed, the moveable member moves from an engaged position to the use-preventing position and locks into the use-preventing position.

6. The single-use oximetry sensor of claim 5, wherein the pin penetrates the movable member.

7. The single-use oximetry sensor of claim 5, wherein when the single-use connector is engaged the movable member moves from an initial position to the use-preventing position.

8. The single-use oximetry sensor of claim 5, wherein the movable member is not penetrated by the pin.

9. The single-use oximetry sensor of claim 5, wherein the locking mechanism is between the movable member and a back face of the housing.

10. The single-use oximetry sensor of claim 5, wherein the housing is of unitary construction to prevent a user from opening the housing and unlocking the movable member from the use-preventing position.

11. The single-use oximetry sensor of claim 5, wherein the moveable member is capable of moving substantially parallel to the back face within the housing.

12. The single-use oximetry sensor of claim 5, wherein the movable member is moved from the engaged position to the use-preventing position via a spring force exerted by a spring mechanism.

13. The single-use oximetry sensor of claim 12, wherein the spring mechanism is between the movable member and a back face of the housing.

14. The single-use oximetry sensor of claim 12, wherein the spring mechanism is integral with the locking mechanism.

15. The single-use oximetry sensor of claim 14, wherein the spring mechanism and locking mechanism are between the movable member and a back face of the housing.

16. A single-use pulse oximetry sensor comprising:
   a sensor comprising a light source and a light detector; and
   a single-use connector electrically connected to the sensor via a cable comprising one or more wires;
   wherein the single-use connector comprises:
      a housing enclosing:
         a plurality of pins coupled to the one or more wires;
         a moveable member penetrated by the plurality of pins;
         a spring disposed in the housing to bias the moveable member towards a connecting end of the single-use connector;
         a locking mechanism disposed between the connecting end of the single-use connector and an initial position of the moveable member; and
      wherein upon an initial engagement of the single-use connector with a complementary connector, the moveable member moves from the initial position to an engaged position in a direction away from the connecting end and compresses the spring, such that when the single-use connector is disengaged from the complementary connector, the spring moves the moveable member towards the connecting end, past the initial position, to a use-preventing position so that the locking mechanism locks the moveable member in the use-preventing position.

17. The single-use pulse oximetry sensor of claim 16, wherein the locking mechanism comprises a latch configured to abut against a side of the moveable member.

18. The single-use pulse oximetry sensor of claim 16 wherein the single-use connector is a male single-use connector for use with a complementary female connector comprising a receiving socket;
   wherein when the moveable member is in the engaged position, the pins are electrically coupled to the receiving socket; and
   wherein when the moveable member is in the use-preventing position, the pins are electrically disconnected from the receiving socket.

* * * * *